United States Patent
Gross et al.

[11] Patent Number: 5,807,375
[45] Date of Patent: Sep. 15, 1998

[54] ANALYTE-CONTROLLED LIQUID DELIVERY DEVICE AND ANALYTE MONITOR

[75] Inventors: Joseph Gross; John Gerard Kelly, both of Dublin, Ireland

[73] Assignee: Elan Medical Technologies Limited, Athlone, Ireland

[21] Appl. No.: 556,744

[22] Filed: Nov. 2, 1995

[30] Foreign Application Priority Data

Nov. 4, 1994 [IE] Ireland ........................... 940864

[51] Int. Cl.$^6$ ............... A61K 9/32; A61M 31/00; A61B 5/05
[52] U.S. Cl. ............ 604/890.1; 604/66; 128/632; 128/635
[58] Field of Search ................. 604/65, 66, 67, 604/131, 132, 133, 890.1, 892.1; 128/632, 635, 642, DIG. 12, DIG. 13

[56] References Cited

U.S. PATENT DOCUMENTS

| | | |
|---|---|---|
| 2,408,323 | 7/1946 | Lockhart et al. . |
| 2,576,951 | 12/1951 | Lockhart et al. . |
| 3,837,339 | 9/1974 | Aisenberg et al. . |
| 4,340,458 | 7/1982 | Lerner et al. . |
| 4,396,464 | 8/1983 | Giner et al. . |
| 4,515,584 | 5/1985 | Abe et al. . |
| 4,627,445 | 12/1986 | Garcia et al. . |
| 4,637,403 | 1/1987 | Garcia et al. . |
| 4,684,365 | 8/1987 | Reinicke . |
| 4,697,622 | 10/1987 | Swift et al. . |
| 4,902,278 | 2/1990 | Maget et al. . |
| 4,953,552 | 9/1990 | DeMarzo . |
| 4,970,145 | 11/1990 | Bennetto et al. . |
| 5,070,886 | 12/1991 | Mitchen et al. . |
| 5,079,421 | 1/1992 | Knudson et al. . |
| 5,122,456 | 6/1992 | Bennetto et al. . |
| 5,160,418 | 11/1992 | Mullen . |
| 5,165,407 | 11/1992 | Wilson et al. . |
| 5,193,545 | 3/1993 | Marsoner et al. . |
| 5,227,042 | 7/1993 | Zawodzinski et al. . |
| 5,231,028 | 7/1993 | Mullen . |
| 5,286,362 | 2/1994 | Hoenes et al. . |
| 5,298,022 | 3/1994 | Bernardi . |

(List continued on next page.)

FOREIGN PATENT DOCUMENTS

| | | |
|---|---|---|
| 0 098 592 | 1/1984 | European Pat. Off. . |
| 0 209 677 | 1/1987 | European Pat. Off. . |
| 0 401 179 | 12/1990 | European Pat. Off. . |
| WO 95/10223 | 4/1995 | WIPO . |
| WO 95/13838 | 5/1995 | WIPO . |
| WO 96/25089 | 8/1996 | WIPO . |
| WO 96/25088 | 8/1996 | WIPO . |

*Primary Examiner*—Mark Bockelman
*Assistant Examiner*—A. T. Nguyen
*Attorney, Agent, or Firm*—Kathleen L. Maher

[57] ABSTRACT

A liquid delivery device comprising a housing having a lower surface for application to the skin of a subject and having a reservoir and a gas generation chamber therein separated by a displaceable membrane. Gas generated by an electrolytic cell under the control of a microprocessor causes the gas generation chamber to expand and the reservoir to contract, thereby discharging a liquid drug, such as insulin, from the reservoir via a hollow delivery needle extending from the lower surface. The delivery needle and a sensor needle both extend from the lower surface a sufficient distance so as to penetrate through the epidermis and into the dermis when the housing is pressed against the skin. The sensor needle has an enzymatic coating for the detection of an analyte, such as glucose in the subject's plasma. The delivery needle is made of platinum-iridium, and a current passes between the needles and a potentiostat circuit according to the amount of glucose detected. A reference electrode (silver/silver chloride) which rests against the subject's skin increases the accuracy of the glucose measurement. The current through the potentiostat circuit is measured by a voltmeter and a signal from the voltmeter is amplified and communicated to the microprocessor which determines the correct rate of delivery of the drug on the basis of the level of analyte detected in the subject's plasma.

22 Claims, 10 Drawing Sheets

U.S. PATENT DOCUMENTS

| | | |
|---|---|---|
| 5,322,063 | 6/1994 | Allen et al. . |
| 5,387,328 | 2/1995 | Sohn . |
| 5,390,671 | 2/1995 | Lord et al. . |
| 5,391,250 | 2/1995 | Cheney, II et al. . |
| 5,399,245 | 3/1995 | Fedkiw, Jr. . |
| 5,422,246 | 6/1995 | Koopal et al. . |
| 5,425,361 | 6/1995 | Fenzlein et al. . |
| 5,443,701 | 8/1995 | Willner et al. . |
| 5,497,772 | 3/1996 | Schulman et al. . |
| 5,515,848 | 5/1996 | Corbett, III et al. . |
| 5,543,024 | 8/1996 | Hanazato et al. . |
| 5,545,143 | 8/1996 | Fischell . |
| 5,547,467 | 8/1996 | Piquett et al. . |
| 5,562,613 | 10/1996 | Kaldany . |
| 5,567,290 | 10/1996 | Vadgama et al. . |

ANALYTE-CONTROLLED LIQUID DELIVERY DEVICE AND ANALYTE MONITOR

FIELD OF THE INVENTION

This invention relates to devices for the delivery of liquid drugs to a subject via the subject's skin, and in particular to "closed loop" insulin delivery devices, as well as to analyte sensors for use in "closed loop" and "open loop" delivery systems.

BACKGROUND OF THE INVENTION

Conventional therapy for insulin-dependent diabetes mellitus involves self-administered subcutaneous insulin injections a number of times daily (usually two, three or four times). The dosage regime is designed to maintain the blood glucose level (glycemia) of the subject between hypoglycemic and hyperglycemic levels, preferably between 3 and 10 mmol/l, taking into account variations arising as a result of, for example, glucose intake at mealtimes and glucose elimination during periods of activity.

In order to provide better control of a subject's glycemia, continuous infusion pumps have been developed to deliver glucose at a basal rate. This rate may be pre-programmed, or the patient or physician may manually control the rate according to the results of successive blood glucose tests (which can be carried out by the patient using apparatus which provides a result within a matter of minutes). The basal rate is usually supplemented by bolus injections before meal times. Such pumps are known as "open loop" systems.

A subcutaneous catheter is used to deliver insulin from an infusion pump to the patient. The open wound caused by the catheter means that the catheter must be resited every few days. Complications arising from the use of the catheter can include erythemia, abscesses, cellulitus and, occasionally, systemic infection.

Implantable devices are also known. Such devices are generally implanted in the abdomen. Complications arising from the use of implantable devices include infection, particularly of the implantation site, and skin necrosis over the implant.

"Closed loop" systems comprise an insulin pump controlled by a microprocessor and a glucose sensor linked to the microprocessor. The rate or frequency of insulin administration is controlled by the microprocessor according to the instantaneous blood glucose level measured by the sensor. Because a system of feedback similar to natural homeostatic regulation is used, a closed loop insulin delivery system may also be referred to as an "artificial pancreas".

In general, closed loop systems are not implanted. Many of the known systems are of the so-called bedside type which include a reservoir and a pump for a hypoglycemic agent (such as insulin), a reservoir and pump for a hyperglycemic agent (such as glucagon or glucose), means for injecting each agent into the body, means for measuring the blood glucose levels, means for controlling the delivery of each agent at a rate determined by the measured blood glucose level and a housing containing the reservoirs, pumps, measuring apparatus and controlling means. The size of this type of artificial pancreas means that it is limited to bedside use (which explains the name). Furthermore, because the means for measuring blood glucose levels requires the collection of blood from the patient, this mode of therapy imposes a heavy burden on the patient, so that it is impossible to use the device continuously for a long period of time.

A portable artificial pancreas is known from EP-A-0 098 592. The artificial pancreas has a reservoir for a blood sugar control agent and a feed pump adapted to inject the control agent into the subject's body at a rate determined by a microcomputer. The microcomputer receives a signal from a glucose sensor which is inserted into the subject's body, and calculates the required insulin delivery rate from the detected glucose level. The glucose sensor and the injection unit (which includes the reservoir, the pump and the microcomputer), are separate from one another and the output signal of the sensor is transmitted to the microcomputer by radio.

In the preferred embodiment, a detection unit, including the sensor and radio transmitter, is in the form of a wristwatch having a tube leading therefrom to a catheter which has the blood glucose sensor at the end thereof. The injection unit, which includes a radio receiver for receiving the signal from the detection unit, is adapted to be worn on a belt.

This type of portable artificial pancreas shares the problems associated with open loop systems (i.e. erythemia, abscesses, cellulitus and systemic infection), but the problems are, in fact, magnified because two catheters are used instead of one.

Apart from the strictly medical problems associated with existing pumps, a significant amount of pain and trauma is also associated with the application of known devices when the catheter(s) is/are inserted into the skin.

Furthermore, such devices are inconvenient to use and may cause discomfort as the pumps are often quite bulky and are generally worn on a belt or a shoulder strap, as is the case with the injection unit of EP-A-0 098 592.

Although implantable devices have found a limited success in open loop systems, they are unsuitable for use in closed loop systems as a failure of the sensor pump, or controlling equipment, or the blockage of an outlet (which might occur as a result of a build-up of fibrin, for example), can lead to ketoacidosis. A patient using an open loop system will be supplementing the basal rate with bolus injections and may be carrying out regular blood glucose tests as before. According, there is far less danger of severe hypoglycemia or hyperglycemia occurring if an implanted open loop system fails than would be the case for a patient with an implanted closed loop system.

Portable closed loop systems, such as the system described in EP-A-0 098 592, require a reliable glucose sensor. The sensor employed in EP-A-0 098 592 comprises a platinum electrode and a silver electrode. The platinum electrode and silver electrode form part of an electric circuit in which hydrogen peroxide is electrolysed. The hydrogen peroxide is produced as a result of the oxidation of glucose on a glucose oxidase membrane, and the current through the circuit provides a measure of the hydrogen peroxide concentration, and hence the glucose concentration, in the vicinity of the sensor.

The sensor is in the form of a composite electrode comprising both the platinum and silver electrodes, a glucose oxidase membrane layer, a polyurethane film which is permeable to glucose, oxygen and hydrogen peroxide, and a steel, glass and plastics supporting structure. The composite electrode is attached to the forward end of the catheter which is inserted into a blood vessel or beneath the skin of the subject.

The accuracy of the electrode (and accordingly, the accuracy of the controlled delivery of insulin or glucagon) depends on the efficient conversion of glucose and oxygen to give gluconic acid and hydrogen peroxide. The amount of hydrogen peroxide must be reliably linked to the amount of available glucose in the bloodstream. False determinations may, however, arise with the sensor described in EP-A-0 098 592 because all of the available glucose may not be converted by the glucose oxidase enzyme if there is an insufficient supply of oxygen.

Oxygen is available in dissolved form in the blood and it occurs as a product of the electrolysis of hydrogen peroxide. However, the assumption that excess oxygen will be available relative to glucose may not be correct. If oxygen is not available in excess, then the amount of available oxygen (not glucose) will be the limiting factor in the reaction and the current provided by the electrode will provide a false determination of the subject's glycemia.

The ultimate intention of manufacturers of closed loop systems is to devise a system which provides the subject's entire insulin requirement without there being any need for self-injection of bolus insulin. Accordingly, any such system must be acceptable to the patient in terms of being as unobtrusive as possible, being minimally painful and traumatic in application and use, providing minimum discomfort during administration, as well as being of the utmost reliability and efficiency. These objectives are not met by the devices of the prior art, for the reasons outlined above, and it is an object of the present invention to provide a device having the above-mentioned qualities.

A further aspect of the invention relates to a sensor per se for use in conjunction with an open loop system, to provide an indication that the rate of drug delivery should be varied or that a bolus injection should be administered. It can also be used in conventional diabetes therapy to replace the uncomfortable and potentially unreliable and dangerous method of self-administered blood tests at various intervals throughout the day.

One of the primary problems associated with conventional diabetes therapy (i.e. self-injection of insulin, optionally preceded by a blood test) is its susceptibility to human error. A diabetic whose blood level has become unexpectedly hypoglycemic, e.g. as a result of unforeseen or unexpectedly strenuous activity or as a result of prolonged abstinence from sugar-rich nourishment, is in severe danger of entering a hypoglycemic coma. The danger is compounded by the fact that the time lost between onset of hypoglycemic symptoms and an actual comatose state can be very short, and by the fact that hypoglycemia has a profound psychological effect which is superficially similar to drunkenness in that the patient becomes giddy and loses inhibitions and a sense of responsibility. Furthermore, uninformed bystanders may in fact mistake hypoglycemic symptoms for drunkenness.

Bearing the above factors in mind, it would be desirable to provide means by which a patient can ascertain his or her blood glucose level as desired without the inconvenience of obtaining a blood sample and carrying out a blood glucose test.

Another object of this aspect of the invention is the provision of a blood glucose monitor which informs the diabetic (and, optionally, people in the vicinity) that the blood glucose levels are abnormally low or high, as the case may be, thereby allowing the diabetic to take corrective action, such as the intake of a sugar-rich drink, for example or an injection of insulin, depending on whether hypoglycemia or hyperglycemia is indicated.

Bearing in mind that relatively sophisticated and/or costly electronic circuits may be used in such a monitoring device, it is highly desirable to minimise the expense involved in manufacturing the device. This is particularly true in the case of a device employing an enzymatic sensor, since such a sensor will probably have quite a short life span necessitating frequent replacement. Even a significantly advantageous invention, improvement or modification will not achieve its commercial potential if, in the opinion of the consumer the expense is not justified by the advantages.

A further problem associated with enzymatic sensors which are intended for use by patients under real life conditions, as opposed to experimental prototypes, is that of sensor degradation. Even if a sensor is calibrated, it can become damaged, inefficient or inaccurate as a result of incorrect application, abrasion, manufacturing flaws, changes in enzyme activity with time or changes in the transport properties of protective membranes surrounding the sensor due to interactions with foreign materials.

A paper by Rishpon J. (Biotechnology and Bioengineering, Vol. XXIX, pages 204–214 (1987)) deals with improved glucose oxidase enzyme electrodes and provides a method of determining some of the parameters affecting electrode efficiency from the signal obtained. The experiment described uses platinum disc electrodes covered by a glucose oxidase enzyme layer cross-linked to bovine serum albumen. The electrode is initially held for 10 seconds at 0.0 volts and then stepped to 0.8 volts for 10 seconds. This square wave potential pattern is repeated and the current is measured. The current is digitized and fed to a microcomputer every 200 $\mu$s. These individual current readings were averaged to provide improved resolution, but were nevertheless found to give unsatisfactory resolution and signal to noise ratio. Accordingly, the current readings were integrated to provide coulometric rather than amperometric data. This coulometric data was then analysed to provide kinetic and transport parameters relating to the electrodes and it was found that the analysed data could be used in the evaluation of various electrode types.

The present invention seeks to provide a determination of sensor quality or degradation when the sensor is used in vivo on an on-going basis without requiring extensive computations and analysis, and providing direct results rather than abstract parameters such as diffusion coefficients (as obtained by Rishpon).

Yet a further object of the invention is to provide improved signal to noise ratios using direct measurements, without requiring complex multiple measurements, averagings and integrations. In this respect, it should be noted that the background noise in measuring glucose activity may be greatly increased by the presence of materials such as paracetamol which interfere with the accuracy of glucose measurements by the enzymatic sensor. In the amperometric measurements described by Rishpon, unsatisfactory resolution and signal-to-noise ratios were obtained before integration was effected, and it should be noted that each data point on the amperometric graph described by Rishpon as "unsatisfactory" in fact represented the averaging of 2500 distinct measurements.

SUMMARY OF THE INVENTION

Accordingly, the invention, in a first aspect, provides a liquid delivery device for delivering a liquid drug to a subject via the subject's skin at a rate sufficient to maintain plasma levels of an analyte within a physiologically acceptable range, comprising:

a housing having a lower surface for application to the skin of the subject;

means for holding the housing in position with the lower surface against the subject's skin;

a drug reservoir within the housing;

a hollow delivery needle associated with the drug reservoir extending through the lower surface when the lower surface is in contact with the subject's skin, having an inner end communicating with the drug reservoir and an outer end projecting outwards a sufficient distance so as to penetrate through the epidermis and into the dermis when the housing is pressed against the skin;

means for actively discharging the drug from the reservoir to the subject's skin via the needle;

means for detecting the concentration of an analyte in the subject's plasma and for providing an electrical signal in accordance with the detected concentration, the concentration of said analyte being directly or indirectly related to the amount of drug required by the subject; and means for receiving said electrical signal and for controlling the rate of active discharge of drug in response thereto.

The term "liquid" as used herein includes pure liquids, solutions, suspensions, low-viscosity gels and other flowable compositions. The term "drug" includes pharmaceutical, therapeutic, diagnostic and nutritional agents, and compositions containing such agents.

The device according to the invention is far less painful in application and use if suitable needle dimensions are chosen. Preferably, the needle is of a suitable length to penetrate the patient's skin either intradermally (i.e. the tip of the needle extends to a point within the dermis) or subcutaneously (the tip of the needle penetrates through the dermis into the underlying tissue).

The device can be pressed against the skin and this action ensures correct insertion of the needle. If a narrow needle, preferably having an outer diameter of less than 0.2 mm, is used, only the minimum amount of trauma will be associated with the application of the device.

Furthermore, as the manner of insertion of the needle is invariable (the device is pressed against the skin and the needle always penetrates the skin correctly), the subject can personally apply the device without having to take any particular precautions or without having to receive any medical training. This is not the case with the devices of the prior art, which require, for example, catheters to be inserted intravenously or subcutaneously. In conventional insulin therapy, the patient must be taught to administer subcutaneous injections, and if sufficient care is not taken the injection may be intravenous or intramuscular rather than strictly subcutaneous, or the needle may hit a bone under the skin. If the injection is delivered to the wrong environment (vein or muscle), the uptake of drug will not occur at the correct rate. The risks associated with these occurrences are significant drawbacks to known systems.

For the above reasons, the invention provides a significant advantage over known closed loop systems, making it suitable for unsupervised use. As the device also has means for holding the housing in position with the lower surface against the subject's skin, the device is completely portable and may be worn inconspicuously on the body under all clothing without requiring a belt or a bracelet-type strap.

Furthermore, as the device is not a two-part system, as is the case with EP-A-0 098 592, the signal may be communicated directly from the means for detecting the blood concentration of an analyte to the means for controlling the rate of active discharge of the drug. Accordingly, there is no danger of the signal from the sensor being misinterpreted due to radio interference from nearby sources, and the device itself cannot interfere with nearby equipment.

The device is also less expensive to manufacture than the relatively complex portable artificial pancreases of the prior art. It can be disposable and is preferably designed for once-daily administration. Suitably, the device is applied in the morning and worn throughout the day. It may be removed at night or worn throughout the night. If removed, the subject may inject a conventional night-time dose of insulin or the device may be adapted to deliver a suitable bolus of insulin before removal.

Suitably, the delivery needle extends permanently through the lower surface.

Preferably, however, said delivery needle is recessed within the housing when the lower surface is not in contact with the subject's skin, and the device comprises means for extending the delivery needle through the lower surface so as to project outwards said distance when the housing is pressed against the skin. This may be achieved, for example, by means of a mechanical, electrical or piezoelectric sensor located on the lower surface of the housing, with the sensor means for extending the delivery needle through the lower surface being actuated by the sensor. The extension of the delivery needle is carried out in a consistent and suitable manner when this embodiment is used.

Preferably, the delivery needle penetrates through the dermis for subcutaneous delivery of the drug. The choice of intradermal or subcutaneous delivery, however, depends on the condition to be treated, the drug to be used and the chosen therapy and dosage regime. For certain drugs, it is preferable to deliver dosages intradermally as a depot effect may be desired, i.e. the drug builds up in concentration within the skin layers and is gradually released therefrom to the systemic circulation. With suitable drugs this depot effect can provide therapeutically effective blood levels many hours after the device has been removed.

According to a further embodiment of the invention, the means for detecting the plasma concentration of the analyte comprises a sensor needle extending from the lower surface of the housing when the lower surface is in contact with the subject's skin, the sensor needle having an outer end projecting outwards a sufficient distance so as to penetrate through the epidermis and into the dermis when the housing is pressed against the skin.

Thus, the application of the housing can ensure the insertion of both the delivery needle and the sensor needle for the analyte. This is particularly advantageous for the reasons recited above in relation to the delivery needle.

Suitably, the sensor needle extends permanently through the lower surface.

Preferably, the sensor needle is recessed within the housing when said lower surface is not in contact with the subject's skin, and the device comprises means for extending the sensor needle through the lower surface so as to project outwards said distance when the housing is pressed against the skin.

The same means may be used to extend both the delivery needle and the sensor needle simultaneously through the lower surface when the device is pressed against the skin. Alternatively, each needle may be activated separately as the particular parts of the housing adjacent to the point through which the needles extend comes into contact with the skin.

Suitably, the sensor needle penetrates through the dermis.

It is envisaged that the same needle may be used for the purposes of delivery and analyte sensing. Preferably, however, the delivery and sensor needles are in spaced apart relationship.

In a preferred embodiment, the delivery and sensor needles are electrically conducting and the means for detecting the concentration of an analyte is to measure an electric current between the needles, the circuit being completed upon application of the lower surface to the skin of the subject. The third reference voltage point kept at a specific voltage compared to the sensor needle an electric circuit comprising a power source connected between the needles, the needles may be entirely formed of conductive material or they may carry a conductive coating or conductive elements therein.

Suitably, the electrical signal provides a measure of the electric current flowing through the circuit.

Suitably, the sensor needle has an enzyme associated therewith, the enzyme being specific to the analyte to be detected and the current through the circuit being dependent on the concentration of a reactant in the enzymatic reaction in the vicinity of the needle.

Preferably, the sensor needle has an enzyme associated therewith, the enzyme being specific to the analyte to be detected and the current through the circuit being dependent on the concentration of a product of the enzymatic reaction in the vicinity of the needle.

The use of an analyte-specific enzyme is particularly advantageous as such an enzyme can be used to detect minute concentrations of analyte in the blood, plasma or tissue of the subject. The association of an electric current with the enzymatic reaction allows a quantitative evaluation of analyte concentration. The electrical current may, of course, be amplified or analysed as appropriate by means of any one of a vast range of electronic techniques. Furthermore, the enzyme allows high concentrations of analyte to be measured equally accurately as only a very small quantity of enzyme can catalyse large amounts of substrate (analyte). Some pure enzymes, for example, can catalyse the transformation of as many as 10,000 to 1,000,000 mols of substrate per minute per mol of enzyme. Accordingly, only a very small enzyme supply needs to be associated with the needle to ensure total analyte reaction in the vicinity of the needle.

Preferably, the product of the enzymatic reaction is a charged species, or said product spontaneously breaks down to produce a charged species, or said product reacts catalytically at the surface of the needle to produce a charged species. The term "charged species" as used herein includes ions, protons and electrons. In any of these situations, the production of charged species in the vicinity of the needle allows a current to flow between the electrodes. Accordingly, the current through the circuit is dependent on the numbers of charged species available to carry current at any time.

Suitably, the product of the enzymatic reaction or a derivative thereof partakes in an electrochemical reaction, the sensor needle acting as one electrode of an electrochemical cell and the delivery needle acting as another electrode. In accordance with Faraday's Laws of Electrolysis, the amount of a substance consumed at an electrode of an electrochemical cell is directly proportional to the current through the cell. Obviously, one would not expect this strict relationship to hold for an electrochemical cell incorporating a complex biological system, but the circuit can nevertheless be calibrated to provide a correlation between the current and the analyte concentration.

Suitably, when the enzymatic reaction requires free oxygen to proceed, the structure of the sensor needle allows oxygen to pass from an inner end thereof which is in communication with a supply of oxygen to the exterior surface of that part of the sensor needle which projects from the housing.

Preferably, the needle is a hollow needle open at the outer (skin-penetrating) end to provide communication between the inner end and the enzyme.

The use of a hollow needle (or of some other structure of needle which allows oxygen to reach the location of the enzyme) confers an important advantage over conventional implanted enzyme sensors, as the hollow needle ensures that the rate of reaction is never restricted by a lack of oxygen. The supply of oxygen may be air inside the housing, air outside the housing, an oxygen reservoir within the housing or an oxygen source (such as an electrochemical cell) inside the housing, to provide a few examples.

Preferably, the enzyme is in the form of an enzyme-containing coating on the surface of the needle.

Further, preferably, the enzyme-containing coating is covered by a protective coating of an analyte-permeable material.

Suitably, said analyte-permeable material is a perflourinated ion-exchange membrane, for example, "Nafion" ("Nafion" is a Trade Mark). This type of material protects the enzyme before and during operation of the device. If the sensor is in the form of a hollow needle, the coating may cover the open end of the needle to prevent fluids from entering the needle.

According to a preferred embodiment, the analyte is glucose, and the drug is selected from glucagon and insulin or analogues thereof.

The insulin used in the device may be chosen to meet the requirements of the patient. It may be bovine, porcine, human or synthetic and it may be short acting or long acting, or it may comprise a mixture of different types of insulin.

Preferably, in this preferred embodiment of the invention, the enzyme is glucose oxidase.

Further, preferably, the product is hydrogen peroxide.

In the preferred embodiment, the hydrogen peroxide is catalysed to produce oxygen, hydrogen ions and electrons and the magnitude of the current through the circuit is related to the number of electrons produced.

Suitably, the hydrogen peroxide is produced adjacent to a platinum supply, the platinum supply catalysing the oxidation of the hydrogen peroxide. The platinum may be in a colloidal dispersion within a coating on the surface of the sensor needle, it may be carried by particles distributed in intimate admixture with the enzyme supply, it may be provided on the surface of the sensor needle, or the sensor needle may comprise platinum or a platinum alloy such as platinum-iridium.

A high degree of accuracy may be achieved if the electric circuit comprises a reference electrode which is adapted to contact the subject's skin and the sensor needle is biased at a fixed potential with respect to the reference electrode.

Suitably, the electric circuit comprises a potentiostat having an operational amplifier which drives a current between the sensor and delivery needles.

Further, preferably, the power source and the sensor needle are connected in series with the positive input of the amplifier, and a resistor and the delivery needle are connected in series with the amplifier output, the reference electrode being connected to the negative input of the amplifier.

As will be further described below, the potentiostat maintains the potential of the sensor needle at a preset level with respect to the reference electrode by passing the current between the sensor needle and the delivery needle. Thus, the sensor needle acts as a working electrode and the delivery needle acts as a counter electrode.

The current through the reference electrode is, in a well calibrated potentiostat, minimal and the current between the working electrode and the counter electrode is independent of the resistance in the "cell" (in this case the skin and tissue between the needles). Thus, the current is limited by the numbers of mobile charged species available to carry current.

Suitably, the current through the circuit is determined by measuring the voltage drop across the resistor.

Preferably, a voltmeter connected across said resistor provides a signal determined by the magnitude of the voltage drop and the signal is amplified and supplied to the means for receiving an electrical signal and for controlling the rate of active discharge of drug in response thereto.

Further, preferably, said means for controlling the rate of active discharge is a pre-programmable microprocessor which calculates the required drug dosage from the received signal and which controls the rate of active discharge in order to provide the required dosage.

Optionally, the circuit comprises switching means to allow current to flow intermittently. In this embodiment, the time taken for the current to reach a steady state (if a steady state is reached) can be analysed to determine information regarding the operation of the device. Suitably, therefore, a charge accumulates at the sensor needle when current is prohibited and the charge disperses when current flow begins.

An explanation of how a pulsatile current can be used to derive useful information on transport and kinetic parameters is given in the paper by J. Rishpon referred to above. By using a voltage stepped periodically between 0.0V (10 seconds) and 0.8V (10 seconds) and observing the resultant current specifically by sampling the current at intervals of 200 $\mu$s and integrating the digitized signal to obtain a chronocoulometric response, sensitivity was greatly increased above that available by steady-state measurements. However, sophisticated equipment including a microcomputer was required to digitize, average and integrate the current measurements.

Preferably, the switching means comprises means for intermittently applying a voltage to the sensor needle. Suitably, the voltage is applied as a stepped voltage. As the enzymatic reaction proceeds independently of the current, a charge will accumulate at the sensor needle when the current is switched off. When the current is switched on, the charge is able to disperse, and the current takes the form of a peak which falls away to a steady state level.

Preferably, the current is measured immediately after the stepped voltage is applied. This enables a large current to be measured and improves the signal to noise ratio.

In a preferred embodiment, the circuit further comprises means for comparing the current at different times. This information can be used to evaluate the efficiency and condition of the electrode. In one embodiment, the current is measured twice at times $t_1$ and $t_2$ as it falls from a peak level towards a steady state level, given value $I(t_1)$ and $I(t_2)$. The ratio $I(t_1)/I(t_2)$ has been found to be a constant which is specific to the electrode and which is independent of the concentration of the analyte being measured. It is also been found that for any given construction of electrode, the ratio will remain constant as long as the electrode is functioning correctly, but when the ability to detect glucose is impaired, the ratio will change. Therefore, repeated measurements of this ratio provide a way of monitoring the quality of the sensor over time and the user can thereby be alerted when the sensor requires replacement.

To facilitate the application of the device, in a preferred embodiment, the lower surface is shaped such that when it is pressed against the skin a substantial proportion of the pressure applied to the skin is directed through the needle tip. Thus, the needle may project permanently from a suitable part of the lower surface or it may be extended from a suitable part of the lower surface when the lower surface is pressed against the skin. Preferably, the shape of the lower surface is adapted to compensate for the elasticity of the skin by the design of the lower surface. Generally, this means that the lower surface is shaped such that a substantial portion of the pressure is directed through the tip of the needle itself rather than through the skin-contacting parts of the lower surface, at least while the housing is being pressed against the skin.

Suitably, for example, the lower surface of the housing may have a convex shape and the hollow needle may extend from the centre of the convexity, or the lower surface may be provided with a protuberance from which the needle projects, or the lower surface may be of a conical shape with the needle extending from the apex of the cone (suitably, this is an inverted cone with a large base-to-height ratio).

Preferably, the means for affixing the housing in position comprises a pressure-adhesive coating on the lower surface thereof. This allows the device to be far less obtrusive than the sort of device which must be worn on a belt, shoulder strap or bracelet.

Suitably, the delivery and/or sensor needle(s) project outwards of the housing by 0.3–3.0 mm and have an outer diameter of 0.05–0.4 mm, preferably 0.1–0.3 mm, and an inner diameter of 0.02–0.1 mm, preferably 0.05–0.075 mm. Such needle dimensions allow for intradermal or subcutaneous delivery and a small outer diameter ensures that the application of the needle(s) is relatively painless.

In a preferred embodiment of the invention the reservoir is in the form of an expansible-contractible chamber which is expanded when filled with the drug and which can be contracted to dispense the drug therefrom. Suitably, the drug reservoir, when filled, has a volume of the order of 0.2 ml to 10.0 ml.

Further, preferably, the means for actively discharging the drug comprises an electrically controlled gas generator within the housing for generating a gas to contract the drug reservoir in order to discharge the drug therefrom. Suitably, the gas generator is an electrolytic cell. The use of an electrolytic cell is preferred as the generation of gas is highly controllable and is suitable for delivering accurate amounts of the drug, as well as for allowing the delivery of drug to be started and stopped substantially instantaneously if pulsatile delivery is required.

As a preferred feature, the device comprises a start button which is depressible in order to energize the gas generator and thereby to start discharging the drug from the drug reservoir.

Suitably, the means for controlling the rate of active discharge comprises an electronic circuit for controlling the time and rate of gas generation, thereby controlling the discharge of the drug from the drug reservoir.

Optionally, the device further comprises a membrane which is permeable to the drug and impermeable to solid impurities, the membrane covering the inner end of the delivery needle.

The invention provides, in a second aspect, a device for monitoring the concentration of an analyte in the plasma of a subject, comprising:

a housing having a lower surface for application to the skin of the subject;

means for holding the housing in position with the lower surface against the subject's skin;

an electrical detection circuit comprising a power source connected across two electrodes mounted on said lower surface, the circuit being completed upon application of the lower surface to the skin of the subject, one of said electrodes being a sensor needle for penetrating through the epidermis and into the dermis when the lower surface is applied to the skin and having an enzyme associated therewith, said enzyme being specific to the analyte to be detected, and the current through the circuit being directly or indirectly dependent on the concentration of the analyte in the vicinity of the sensor needle; and a communication circuit comprising means for measuring the current through said electrical detection circuit, means for calculating the plasma concentration of the analyte from the measured current and communicating means for communicating the calculated concentration to the subject.

The application of such a device is no more painful, and may, in fact, be less painful, than a conventional pin prick blood test. Unlike such a blood test, however, the device according to the invention need not be repeatedly administered if the blood levels need to be rechecked. The device may, in fact, be worn in place for continual monitoring over a period of, for example, 12 hours, one day, two days or up to one week. The period is generally limited by the exhaustion of, or a decrease in the efficiency of, the enzyme associated with the sensor needle. The presently preferred frequency of administration is once-daily as this ensures that the sensor needle is always in optimum condition and it also allows the subject to change the site of application regularly.

Suitably, the enzyme is glucose oxidase and the analyte to be measured is glucose.

The invention is not, however, limited solely to glucose monitoring devices. Similar enzymatic sensors may suitably be employed if alternative analytes require monitoring.

According to a preferred embodiment, the sensor needle is a working electrode and the other of said two electrodes is a counter electrode in the form of a platinum surface for contact with the subject's skin.

Although the counter electrode can be an invasive electrode (i.e. a needle) there is no necessity in the present case for a second needle, and in the interests of comfort, it is preferred to employ a counter electrode which rests against the skin. Preferably, the area of such an electrode is maximised to increase sensitivity. In certain cases, the sensitivity of an electrode resting against the skin may not be sufficient, and, accordingly, an invasive needle may be used.

Preferably, the electrical detection circuit also comprises a reference electrode on the lower surface of the housing, in the form of a silver/silver chloride surface for contact with the subject's skin, and a potentiostat having an operational amplifier which drives a current between the working electrode and the counter electrode.

Such a circuit operates as hereinbefore described with reference to the embodiments of the invention in its first aspect.

According to a particularly preferred embodiment, the housing comprises a first part and a second part, the first part comprising the lower surface and the electrodes and the second part comprising the power source and the communication circuit.

Suitably, the first part is detachably mounted on the second part, such that the first part can be disposed of and replaced and the second part can be reused a number of times.

When a two-part device is used, the costs can be considerably lower. The first part contains all of the disposable elements (adhesive, electrode coatings, etc.), while the second part contains the reusable elements, such as the electronic components, the communicating means and the power source. Although a power source such as a battery must be replaced periodically, it is a relatively permanent element in comparison to an enzymatic sensor. Long-term batteries can be used having a life span of over two years. Accordingly, such batteries can be reused hundreds of times relative to the first part.

Suitably, the communicating means is activated when the calculated analyte plasma concentration falls outside a predetermined range.

Further, suitably, the communicating means comprises an audible alarm.

Thus, an audible alarm can be made to sound if the subject has blood levels approaching those associated with hyperglycemia or hypoglycemia, and corrective action can be taken before any serious condition develops. Preferably, different sounds are emitted by the alarm depending on the condition of the patient. Furthermore, different sounds or louder sounds can be emitted if the situation worsens.

Preferably, the communicating means operates continuously to provide a constant indication of the subject's analyte plasma concentration.

Further, preferably, the communicating means comprises a visible display of the analyte concentration. Suitably, the visible display is in the form of a liquid crystal display for indicating the analyte concentration as a numerical value.

Other visible displays are, of course, possible, such as a series of light, with a number of lights lit indicating an approximate blood glucose level, or a dial indicating a numerical value relating to the blood glucose level, etc.

One of the most important advantages associated with a device according to the invention is that the patient can check blood glucose levels throughout the day and, through experience, a familiarity can be built up with the patterns of fluctuation in blood glucose level associated with normal daily routine and with extraordinary events such as strenuous exercise, the consumption of different types of foods and drinks and variations in insulin dosage. This will provide a diabetic with an awareness of the effect of various factors on his or her blood glucose levels and preventive action can be taken before it is strictly required. Developing such an association need not be a conscious exercise on the part of the diabetic, because an association of this type is built up through experience.

Heretofore, diabetic subjects have been able to recognise that blood glucose levels should be increased or decreased, but this is generally as a result of the onset of hyperglycemic or hypoglycemic symptoms. By recognising that corrective action is required before such symptoms develop, the blood glucose levels of the subject will be far more regular.

An additional advantage is that a diabetic subject using a device according to the invention will not mistake unrelated symptoms as being related to abnormally high or low blood glucose levels. An objective check is available which prevents the subject from mistakenly increasing insulin or sugar intake.

Although not explicitly enumerated, many of the features of the invention in its first aspect are suitable for incorporation into the second aspect, as will be apparent to the skilled person. Furthermore, both aspects of the invention can be combined to provide a delivery device with monitoring and display features.

In a third aspect, the invention provides a method of measuring the plasma concentration of an analyte comprising the steps of: a) penetrating the epidermis with an enzymatic sensor which forms part of an electrical circuit, wherein the current through the circuit is dependent on the presence of a species produced by the enzymatic reaction with the analyte; b) supplying a periodic potential to the enzymatic sensor such that current only flows through the electric circuit intermittently; and c) measuring the current shortly after it begins to flow.

For the reason indicated above and, as will be further illustrated below, this method has been found to provide accurate results in a far simpler and more efficient manner than the chronocoulometric method known from the prior art.

Suitably, the potential is supplied intermittently as a periodic stepped potential, providing a disconnect period and a connect period, thereby giving rise to a peak current at the beginning of the connect period, falling away towards a steady state current level.

In a presently preferred embodiment, the disconnect period is at least one second long and the connect period is at least 20 microseconds long.

Preferably, the connect period is in the range 20–400 microseconds. More preferably it is in the range 40–80 microseconds.

Further, preferably, the disconnect period is in the range 1–15 seconds, more preferably 5–10 seconds.

These periods have been found to provide good results when used with the type of glucose sensor further described below. The disconnect period should be long enough for a substantial amount of the current-dependent species to build up at the electrode, in order to provide a strong peak current at the beginning of the connect period.

Suitably, the current is measured in the first 15 microseconds of the connect period. Preferably, the current is measured between 0.25 and 10 microseconds after the beginning of the connect period, and most preferably between 0.5 and 3 microseconds after the beginning of the connect period.

By measuring the current early in the connect period, a strong peak current will be obtained, thereby boosting the signal to noise ratio relative to a steady state amperometric measurements. In the method described by Rishpon (supra), measurements were only made every 200 microseconds. It has been found that the best results are obtained if measurements are made well within 200 microseconds of the start of the connect period, as after 200 microseconds the current will have effectively dropped to a steady state level for many constructions of electrode.

As indicated above in relation to the device, preferably, the method further comprises the steps of measuring the current a second time during the connect period, calculating a ratio between the two measured values, and comparing this ratio to a memorised value or range of values to determine whether the sensor is performing normally. Preferably the second current measurement is made when the current has fallen to a steady-state valve.

Suitably, the method also comprises the step of providing an indication that the sensor is defective if the calculated ratio is different to the memorised value or range of values.

This indication can be effected in many ways, preferably by providing a visible or audible alarm.

BRIEF DESCRIPTION OF THE FIGURES

The invention will be further illustrated by the following description of embodiments thereof, given by way of example only with reference to the accompanying drawings, in which.

DETAILED DESCRIPTION OF THE INVENTION

Figure 1:
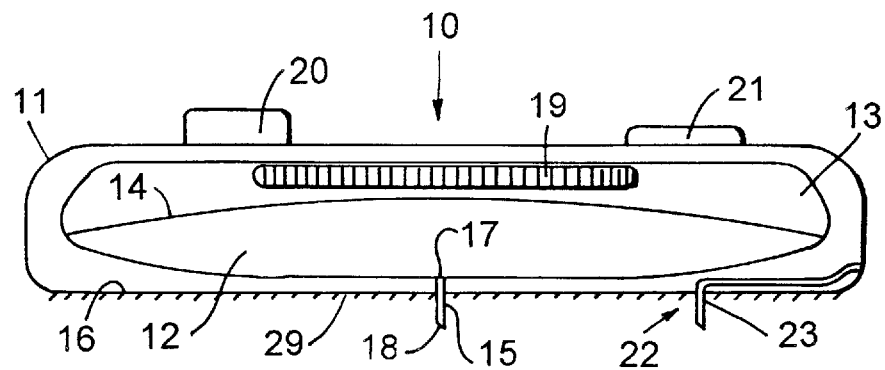
FIG. 1 is a cross-section through a liquid delivery device according to the invention.

FIG. 1 shows a device according to the invention, illustrated generally at 10, for use in the controlled delivery of insulin to a "Type 1" diabetic subject (i.e. suffering from insulin-dependent diabetes mellitus).

The device 10 comprises a housing 11 containing an insulin reservoir 12 for storing insulin in liquid form (suspension, solution or liquid) and a gas generation chamber 13. Reservoir 12 and gas generation chamber 13 are separated by an elastomeric membrane 14, such that an expansion of gas generation chamber 13 leads to a corresponding contraction of insulin reservoir 12.

A platinum-iridium delivery needle 15 projects through a lower surface 16 of housing 11 by a distance of 2.5 mm. Delivery needle 15 is hollow and is open at an inner end 17 to insulin reservoir 12. It is also open at outer end 18 such that, when lower surface 16 of housing 11 is pressed against a subject's skin, delivery needle 15 penetrates through the epidermis and the dermis, thereby establishing communication between insulin reservoir 12 and the subject's subcutaneous tissue via the hollow needle 15. If a shorter needle is used, communication can be established with the capillary system of the dermis.

Gas generation chamber 13 is provided with an electrolytic cell 19 powered by a battery 20 under the control of a programmable microprocessor 21. Microprocessor 21 controls the rate at which gas is generated in electrolytic cell 19 by the electrolysis of water.

Electrolytic cell 19 has walls of a hydrophobic material which allow gas to permeate therethrough but which retain water within the cell. When gas is generated by electrolytic cell 19, the pressure increases in gas generation chamber 13, causing the volume of chamber 13 to expand with a corresponding contraction of insulin reservoir 12, resulting in insulin being forced out of reservoir 12 through needle 15 (and, in use, into the patient's tissue).

Microprocessor 21 controls the rate of gas generation and, consequently, the rate of insulin delivery, by monitoring the patient's blood glucose level by means of a glucose sensor, indicated generally at 22. Sensor 22 comprises a platinum-iridium sensor needle 23 extending from lower surface 16 by about 2 mm.

Figure 2:
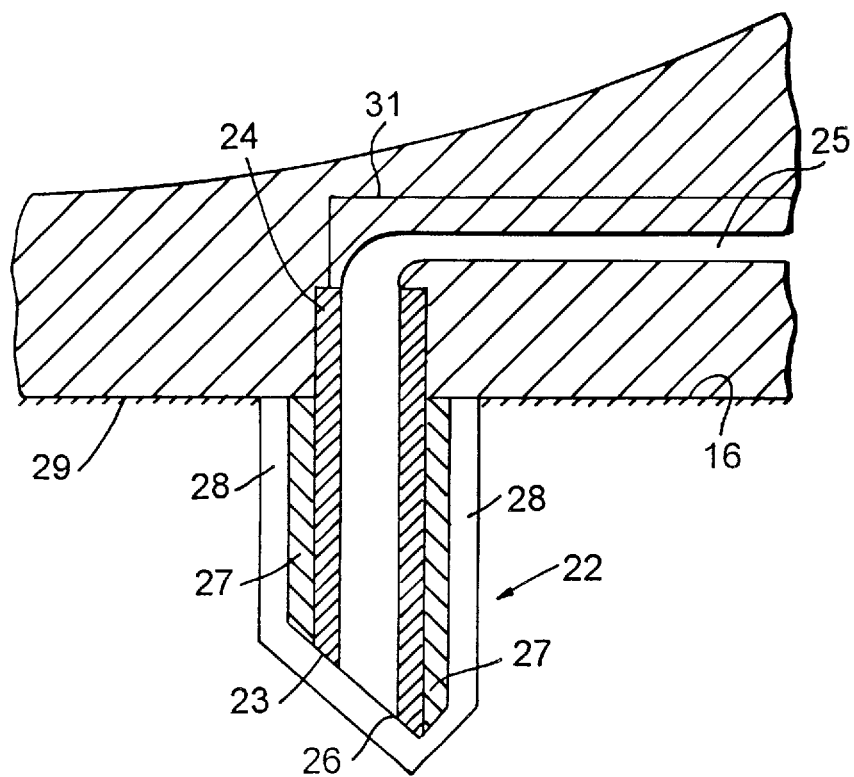
FIG. 2 is a magnified view of a detail of the device of FIG. 1.

Referring additionally to FIG. 2, it can be seen that sensor needle 23 is hollow and is open at both ends. Inner end 24 leads to a passageway 25 extending through housing 11 to the external atmosphere. Accordingly, outer end 26 of sensor needle 23 is, via passageway 25, in communication with a supply of excess oxygen. Needle 23 is coated with a glucose oxidase enzyme coating 27. This entire composite needle structure is covered by a layer of "Nafion" 28 which serves as a protective material, but is permeable to glucose, water, oxygen and hydrogen peroxide. "Nafion" layer 28 also covers open end 26 of stainless steel needle 23, thereby stopping blood from entering and filling the hollow interior of needle 23.

Oxygen within sensor needle 23 can diffuse through "Nafion" coating 28 into glucose oxidase enzyme layer 27. In addition, glucose and water can also diffuse through "Nafion" layer 28 into glucose oxidase enzyme containing layer 27. The enzyme catalyses the reaction of glucose with oxygen and water, producing gluconic acid and hydrogen peroxide. Accordingly, hydrogen peroxide is produced in enzyme layer 27 surrounding platinum-iridium needle 23 in an amount which is directly dependent on the amount of available glucose in the bloodstream.

Delivery needle 15 is a coated with a silver/silver chloride layer. Battery 20 is connected between delivery needle 15 and sensor needle 23 via internal connecting wires 31 (FIG. 2) within the housing. Accordingly, when the needles 15,23 penetrate into the dermis or the subcutaneous tissue, a circuit is closed by the establishment of an electrical connection between the needles 15,23. The circuit is effectively an electrochemical cell, with one electrode being a standard silver/silver chloride electrode in aqueous solution (i.e. needle 23 with its coating immersed in the bloodstream) and the other electrode being a platinum electrode supplied with hydrogen peroxide.

The free mobile charges providing a flow of current through the sensor needle are produced in the catalysed oxidation of hydrogen peroxide on platinum in the reaction:

$$H_2O_2 \rightarrow O_2 + 2H^+ + 2e^-$$

The electrons produced in this reaction allow current to flow through the sensor needle 23.

The current through the circuit is limited by the numbers of electrons available at sensor needle 23. This means that, since the electrons are produced by hydrogen peroxide oxidation and the hydrogen peroxide is produced by the enzymatic oxidation of glucose, that the current depends on the glucose concentration in the bloodstream.

The current through the circuit is amplified and measured by microprocessor 21. Microprocessor 21, which comprises a stored programme, calculates the precise amount of insulin which must be delivered at any time in order to maintain glucose at the optimum physiological concentration.

The microprocessor 21 maintains this concentration by controlling the current flowing through electrolytic cell 19, since any increase or decrease in the amount of gas produced by electrolytic cell 19 results in a corresponding increase or decrease in the amount of insulin injected into the subject via needle 15. In effect, therefore, device 10 acts as an artificial pancreas which continually monitors the glucose concentration in the bloodstream and constantly adjusts the on-going rate of insulin administration to take account of the measured glucose level.

In contrast to prior art devices for the administration of insulin, device 10, which can be affixed to any suitable area of the skin (such as the upper arm or abdomen) is unobtrusive. It is easy and painless to apply; simply by pressing lower surface 16 against the skin, the two needles 15,23 penetrate the skin and an adhesive layer 29, which is provided on lower surface 16, holds the device in place throughout the course of treatment. A device having a diameter of approximately 5 cm and a thickness of approximately 1 cm may contain a sufficient amount of insulin for treatment throughout 12 hours, 1 day, or up to 1 week.

The insulin used in the device may be chosen to meet the requirements of the patient. It may be bovine, porcine, human or synthetic and it may be short acting or long acting, or it may comprise a mixture of different types of insulin.

The needles 15,23, including the coatings thereon, have an external diameter of 0.2 mm. Accordingly, there are no large, open wounds (as there are with traditional delivery cannulas and sensor implants) which may become infected. Additionally, since the site of application can be changed daily, for example, the wounds will heal almost immediately and there is no possibility of either the sensor needle or the delivery needle becoming coated with fibrin.

Figure 3:
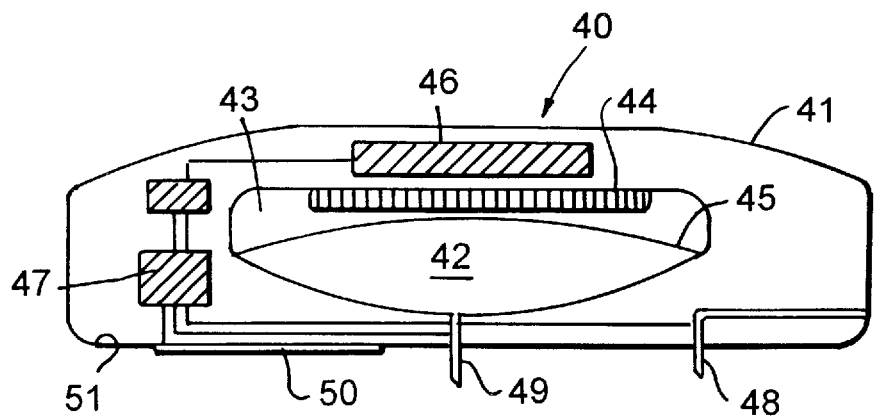
FIG. 3 is a cross-section through a second liquid delivery device according to the invention.

A preferred embodiment of the invention is illustrated in FIG. 3. The device, indicated generally at 40, comprises a housing 41 containing an insulin reservoir 42 and a gas generation chamber 43 within which there is provided an electrolytic cell 44. Reservoir 42 and gas generation chamber 43 are separated by an elastomeric membrane 45 such that when gas is generated by electrolytic cell 44, gas generation chamber 43 expands by displacing membrane 45 downwards and thereby contracting insulin reservoir 42 causing the drug to be discharged therefrom.

Figure 4:
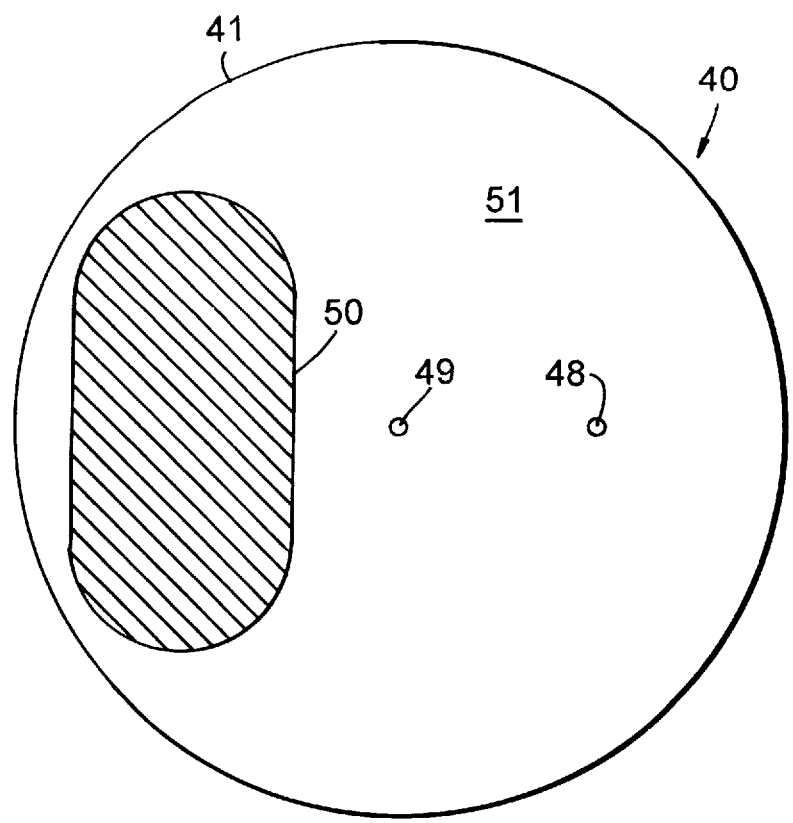
FIG. 4 is a view of the underside of the device of FIG. 3.

The rate of generation of gas is controlled by a microprocessor 46 which receives a signal from a glucose sensing apparatus comprising a potentiostat 47 linked to a sensor needle 48 and a delivery needle 49 of the types described above with reference to FIGS. 1 and 2. The potentiostat is also connected to a reference electrode 50 on the lower (skin-contacting) surface 51 of housing 41. The arrangement of sensor needle 48, delivery needle 49 and reference electrode 50 on lower surface 51 of housing 41 as illustrated in FIG. 4.

Figure 5:
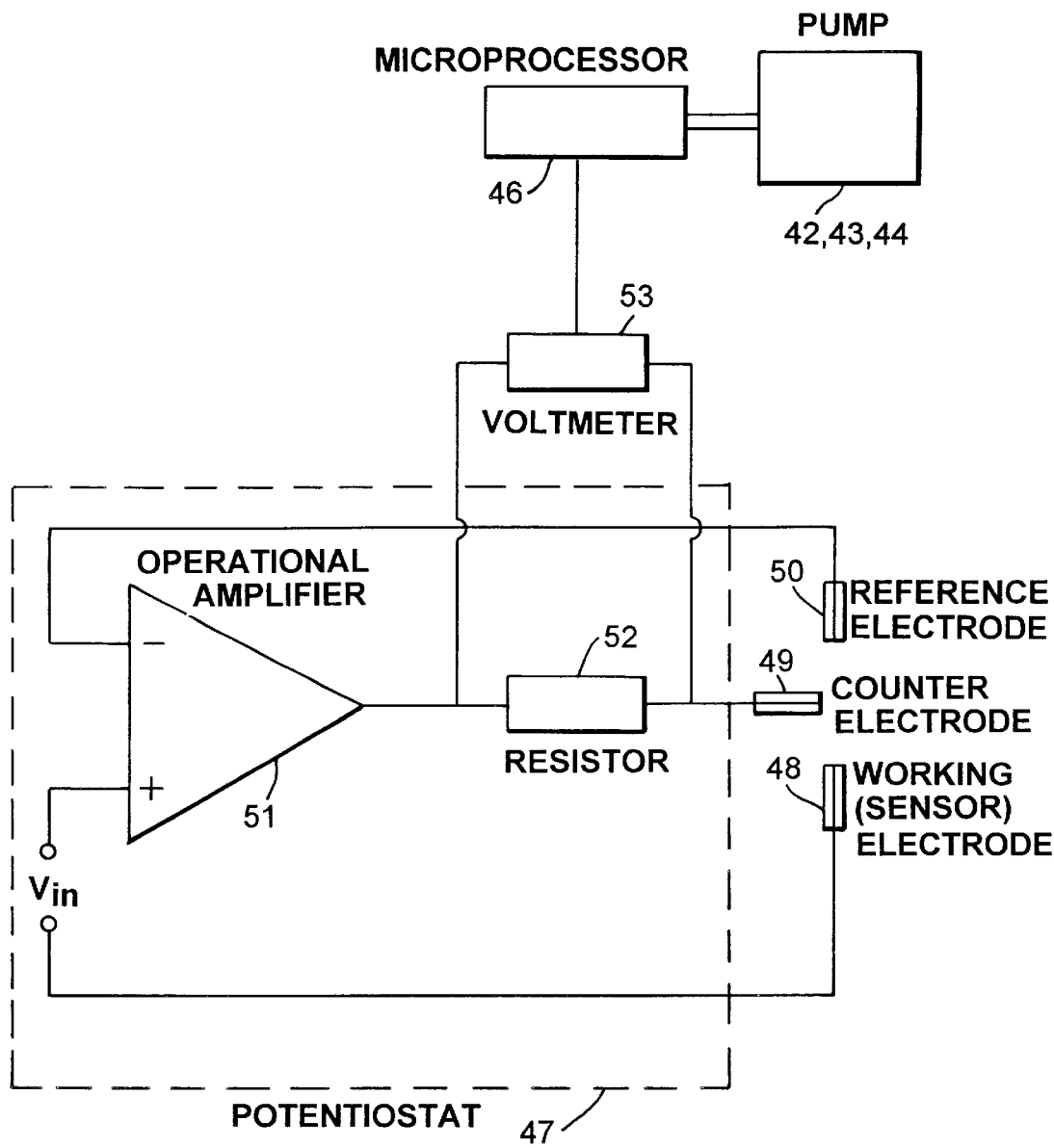
FIG. 5 is a schematic representation of the electronic circuit of the device of FIG. 3.

FIG. 5 is a schematic representation of the electronic circuit of device 40. Potentiostat 47 is shown as a dotted outline. It comprises an operational amplifier 51, a power source (Vin) connected between the positive input of operational amplifier 51 and sensor needle 48 (which acts as the working electrode), and a resistor 52 connected between the output of operational amplifier 51 and delivery needle 49 (which acts as the counter electrode). Reference electrode 50 is connected to the negative input of the operational amplifier 51.

Potentiostat 47 serves to hold the working electrode 48 at a fixed potential relative to the reference electrode. Since both inputs to the operational amplifier are effectively at the same potential, the potential difference between reference electrode 50 and working electrode 48 is equal to Vin. The current through the amplifier 51, which is dependent on the amount of glucose detected by sensor needle 48, is effectively independent of the resistance of the "cell" between working electrode 48 and counter electrode 49, (at least within the operating range of the operational amplifier).

The current is calculated from the voltage drop across resistor 52 using a voltmeter 53 which provides a signal to microprocessor 46 which interprets the signal as indicating a certain glucose concentration in the tissue surrounding sensor needle 48. Voltmeter 53 actually includes both a floating-input voltmeter and an amplifier connected to the output of the voltmeter to provide a signal of suitable strength to microprocessor 46. One or more power sources (not shown) are also included for the purposes of powering electrolytic cell 44 (FIG. 3), the amplifier connected to the voltmeter output, and microprocessor 46. The power source (s) may be that/those used in the potentiostat circuit or separate power source(s) may be provided.

Figure 6:
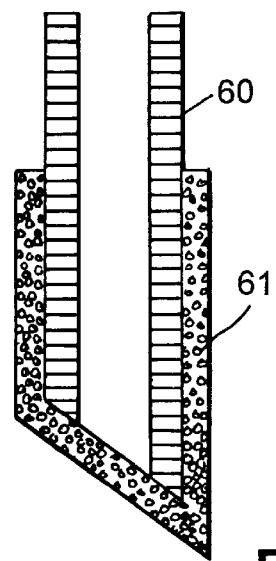
FIG. 6 illustrates an alternative construction of sensor needle for use in a device according to the invention.

An alternative composition of sensor needle to that illustrated in FIG. 2 is shown in FIG. 6. A hollow stainless steel sensor needle 60 has a single coating layer 61 formed from a casting solution of perflourosulphonic acid polymer, such as the perflourinated ion exchange membrane, "Nafion", glucose oxidase enzyme, and a carbon supported catalyst.

Figure 7:
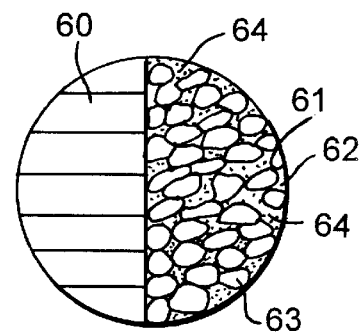
FIG. 7 illustrates a detail of the sensor needle of FIG. 6.

As illustrated in more detail in FIG. 7, the "Nafion" membrane 62 provides an insoluble biocompatible protective matrix for the enzyme 63 retains the enzyme for long term availability in the electrode structure. Membrane 62 also dissolves large quantities of oxygen that is then available adjacent to the enzyme to promote hydrogen peroxide formation for signal generation. The carbon supported catalyst is in the form of platinum-loaded carbon particles 64 having about 10% by weight of platinum. The particles 64 serve two functions: firstly, the catalytic surface for oxidation of hydrogen peroxide is dispersed throughout the matrix layer 62 within which the hydrogen peroxide is generated; secondly, the carbon support for the catalyst provides an electrically conductive path for electrons produced by the oxidation reaction. An electrode having this type of supporting layer is described in U.S. Pat. No. 5,227,042, the disclosure of which is incorporated herein by reference. As U.S. Pat. No. 5,227,042 discloses, other catalysts from the platinum group, such as palladium, ruthenium or rodeium can be used in place of platinum.

Figure 8:
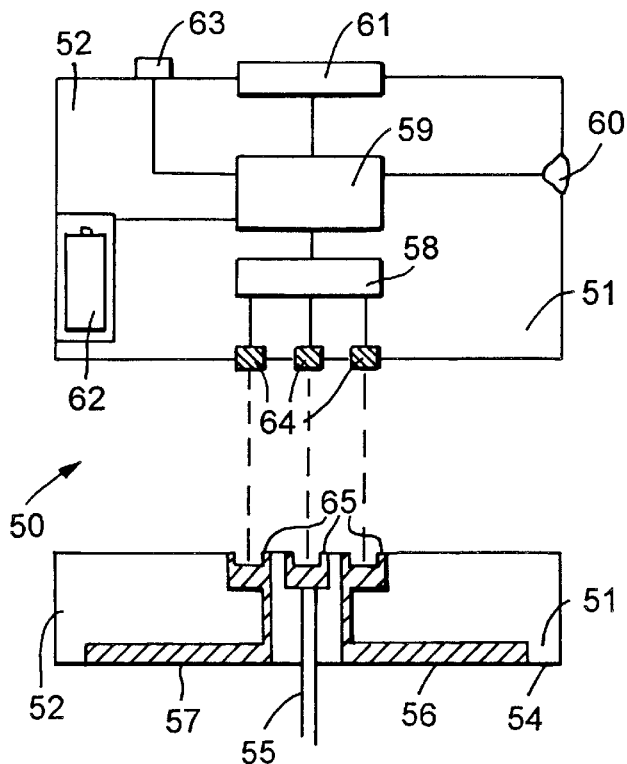
FIG. 8 is a schematic cross section through an embodiment of a device for monitoring plasma glucose levels, according to the second aspect of the invention.

FIG. 8 is a schematic illustration of an embodiment of the second aspect of the invention, namely a device for monitoring the plasma concentration of an analyte. The device, indicated generally at 50, comprises a housing 51 detachable into a first part 52 and a second part 53. The device 50 has a number of features in common with the embodiments of the first aspect of the invention. Specifically, first part 52 of housing 51 has an adhesive lower surface 54 which is provided with a working electrode 55, a counter electrode 56 and a reference electrode 57. The electrodes 55,56,57 are connected to a potentiostat 58 as hereinbefore described.

Working electrode 55 is a platinum-iridium needle coated with a glucose oxidase enzyme coating, as previously described. Counter electrode 56 is in the form of a platinum-iridium surface adapted to rest against the subject's skin and reference electrode 57 is in the form of a silver/silver chloride surface adapted to rest against the subject's skin. As previously described, the current passing between working electrode 55 and counter electrode 56 provides a measure of the glucose concentration in the vicinity of working electrode 55. This current is measured by a microprocessor 59 which is calibrated to allow calculation of the glucose plasma concentration from the measured current through potentiostat 58.

Microprocessor 59 is pre-programmed to activate an audible alarm 60 in the case of hyperglycemia or hypoglycemia. These conditions are recognised by the microprocessor if the calculated glucose concentration rises above or falls below a specific range. Alarm 60 emits different sounds depending on whether hyperglycemia or hypoglycemia is indicated by microprocessor 59. In practice, microprocessor 59 activates audible alarm 60 before the glucose plasma concentration reaches a dangerous level. Thus, the subject, or those supervising the subject, can act in good time by administering glucose-rich food and drink or by administering insulin, as the case may be, before corrective action becomes absolutely critical.

Microprocessor 59 also communicates with a liquid crystal display (LCD) 61 which has seven-segment displays to provide a numerical indication of the level of glucose in the subject's plasma. Thus, if device 50 is worn on a continual basis, the subject can check his or her blood glucose levels at will. In this way, the subject can titrate insulin and/or sugar intake as and when required to provide a plasma glucose profile which more closely resembles that of a healthy individual than that of a self-administering diabetic who self-administers insulin according to traditional criteria (i.e. fixed dosages, variable dosages according to the results of occasional blood tests).

Whereas blood tests prior to insulin administration can allow patients to determine optimum dosages, it is impossible for a diabetic to objectively gauge his or her glucose intake requirements between injections, so the diabetic subject is either confined to a strictly controlled diet or else runs the risk of misjudging a safe level of sugar intake.

Battery 62 powers the device and a start button 63 is provided to activate the device after administration to the skin of the subject.

As illustrated, the device 50 is in two parts 52,53 which are separable from one another. First part 52, which is disposable, comprises the three electrodes 55,56,57 and lower surface 54. As the efficiency of the electrodes will decrease over time (in particular, the dependability of the enzymatic sensor or working electrode 55 will not remain stable indefinitely), it is desirable to replace the electrodes on a regular basis. Second part 53 houses all of the reusable elements of the device. Electrical contact is effected between potentiostat 58 and electrodes 55,56,57 by means of two sets of interengagable contacts 64,65 which fit together when first part 52 is mounted on second part 53. Thus, first part 52 can be replaced daily, for example, whereas second part 53 can be reused indefinitely.

Suitably, battery 62 is a long-term battery which allows second part 53 to operated continuously over two-three years before replacement of battery 62 is necessitated. Microprocessor 59 monitors the power level of battery 62. As battery 62 becomes exhausted, its power decreases and microprocessor 59 activates alarm 60 to provide a special alarm indicating that replacement of battery 62 is necessary.

Push button 63 performs an additional function in that it can be used to reset the alarm when blood glucose levels have moved outside the acceptable range; microprocessor 59 will then only reactivate alarm 60 when calculated glucose levels next move outside the allowable range or, if the levels do not return to normal, when the patient's plasma glucose levels worsen appreciably.

Figure 9:
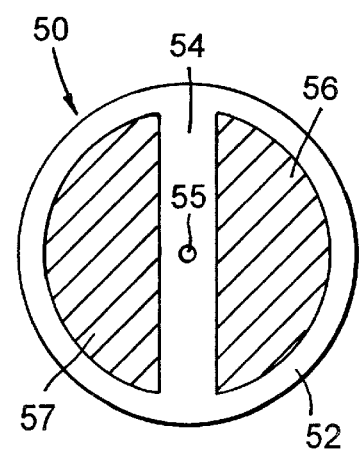
FIG. 9 is a plan view of the underside of the device illustrated in FIG. 8.

FIG. 9 shows a view of the underside of device 50. Thus, lower surface 54 of first part 52 is seen with working electrode 55 (i.e. the enzymatic sensor needle) in the centre.

On either side, two approximately semi-circular surfaces 56,57 are indicated by shaded lines. Surface 56 is the platinum-iridium surface of the counter electrode, while surface 57 is the silver/silver chloride surface of the reference electrode. Lower surface 54 is provided with a suitable adhesive to hold device 50 securely in place against the subject's skin.

Figure 10:
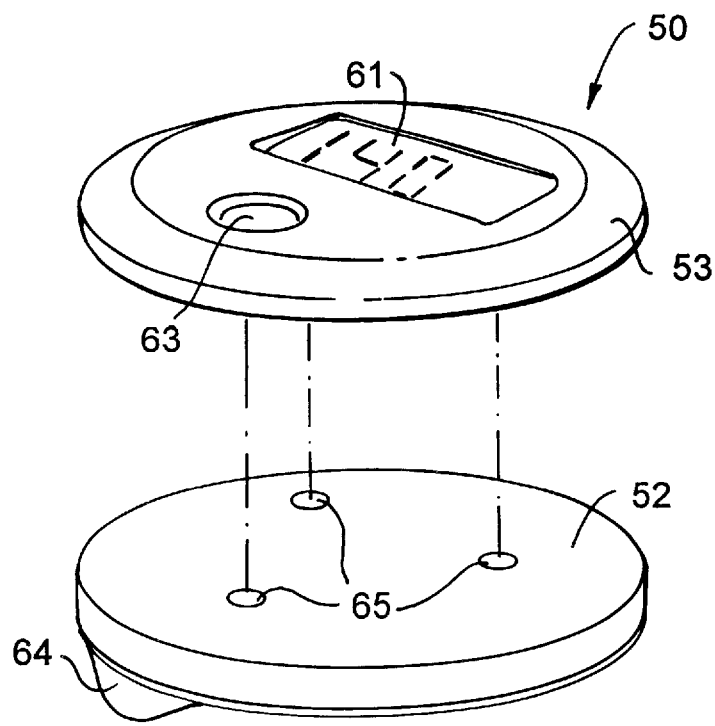
FIG. 10 is a perspective view of an actual device of the type schematically illustrated in FIG. 8, before assembly.
Figure 11:
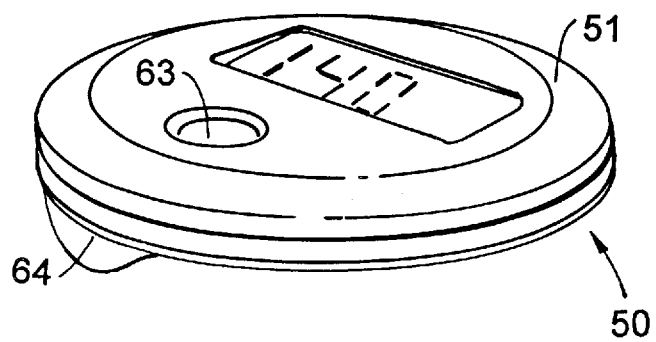
FIG. 11 is a perspective view of the device of FIG. 10 when assembled.

In FIGS. 10 and 11, device 50 of FIGS. 8 and 9 can be seen in perspective view. FIG. 10 shows first and second parts 52,53 before assembly. First part 52 has three contacts 65 on the upper surface thereof which receive three complementary contacts (not shown) on the lower surface of second part 53. As indicated in FIG. 11, second part 53 is provided with a liquid crystal display 61 which gives a numerical indication of the blood glucose levels. Beside LCD 61, push button 63 can be seen. An additional feature which is not illustrated in FIGS. 8 and 9 is a release liner 64 which covers the lower surface (not visible) of first part 52 before use. Release liner 64 is provided both for safety reasons (i.e. to cover the needle before use) and to ensure that the electrode surfaces are undamaged upon application to the skin of the subject.

FIG. 11 shows device 50 when first part 52 has been mounted on second part 53 to form a single housing 51. First and second parts 52,53 are held together by means of a snap action mechanism (not shown). In use, release liner 64 is then removed and housing 50 is present against the surface of the subject's skin such that the sensor needle (not shown) penetrates through the epidermis and into the dermis (depending on the length of the sensor needle, it may also penetrate through the dermis to the subcutaneous tissue) to allow contact between the enzymatic coating on the sensor needle and the subject's plasma. Contact is also effected between the subject's skin and each of the flat electrodes. Operation of the monitoring device begins when push button 63 is pressed. At the end of 24 hours, first part 52 is snapped away from second part 53 and replaced by a new, identical part for monitoring blood glucose levels throughout the subsequent 24 hour/period.

Figure 12:
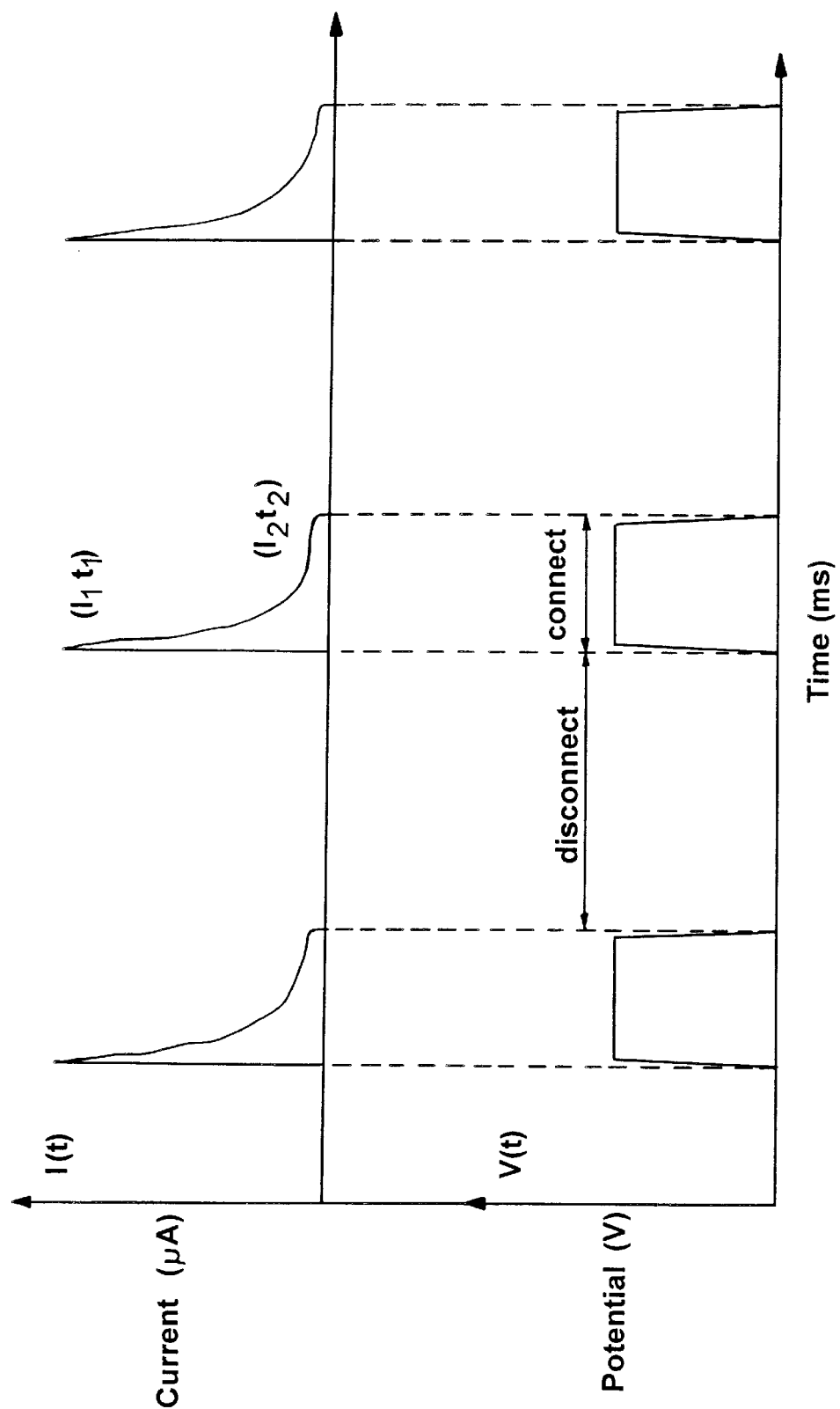
FIG. 12 is a diagram of the potential applied to the sensor electrode and the corresponding current obtained from the electrode.

The operation of the measurement circuit has been described above with the working electrode held at a constant potential above the reference electrode. In a more sophisticated embodiment of the invention, however, a potential is only applied intermittently to the working electrode, as indicated in FIG. 12. From FIG. 12 it can be seen that the potential is stepped between a lower value (preferably 0.0 V) where no current will flow, and a higher value (such as 0.6 V) where current is allowed to flow. FIG. 12 is not to scale and the disconnect period is preferably many times longer than the connect period. In a preferred embodiment, the disconnect period is 3–12 seconds and the connect period is 20–300 microseconds. In the experiments described below, the disconnect period was 7 seconds and the connect period was 60 microseconds.

During the disconnect period, the enzymatic reaction proceeds and hydrogen peroxide builds up at the sensor electrode. Because no potential has been applied and no current is flowing, however, the hydrogen peroxide accumulates continually until the potential is applied allowing a current to flow. As can be seen in the upper half of FIG. 12, the current begins with a peak which then falls away as the hydrogen peroxide is consumed.

Figure 13:
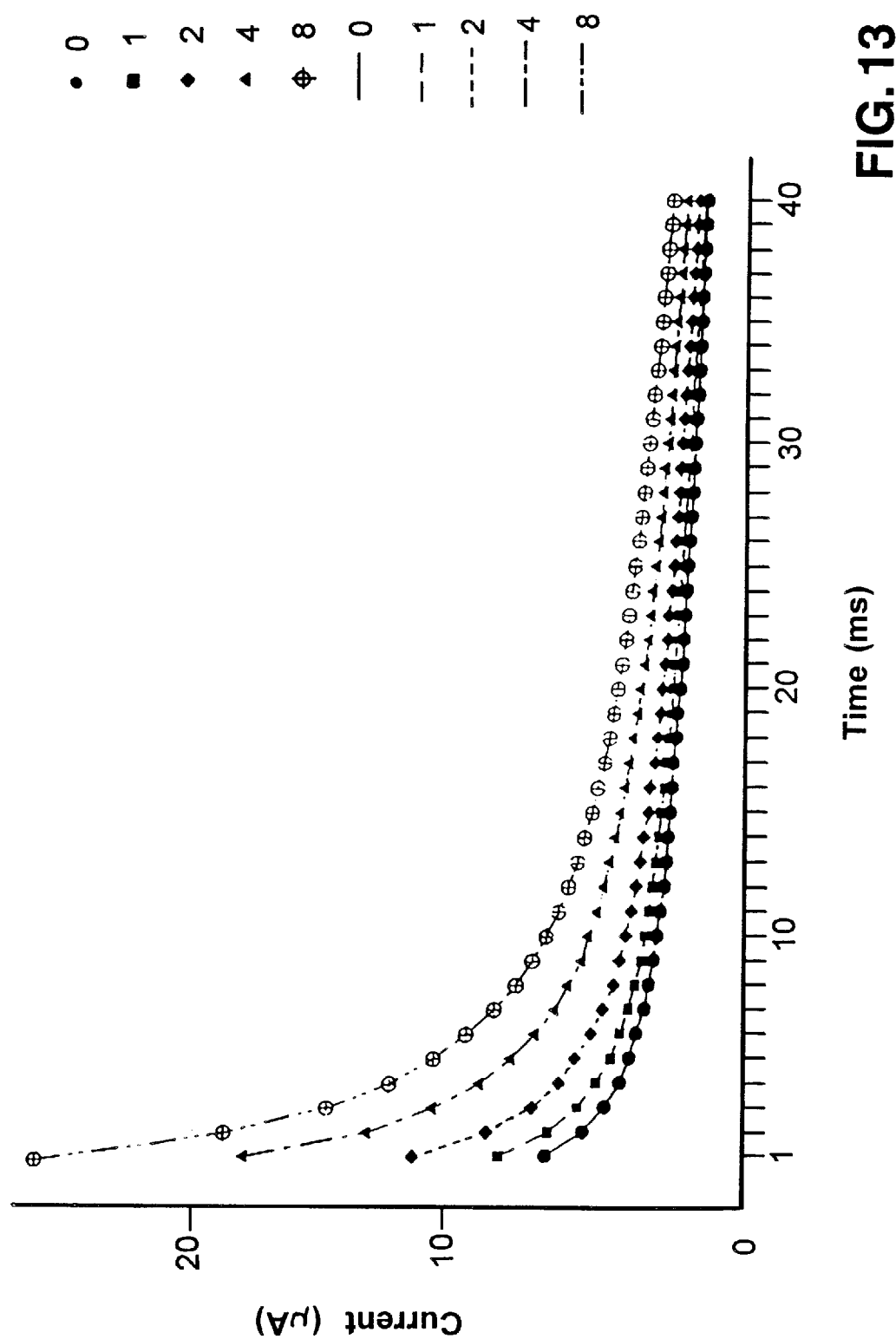
FIG. 13 is a plot of actual current profiles achieved for different glucose concentrations.
Figure 14:
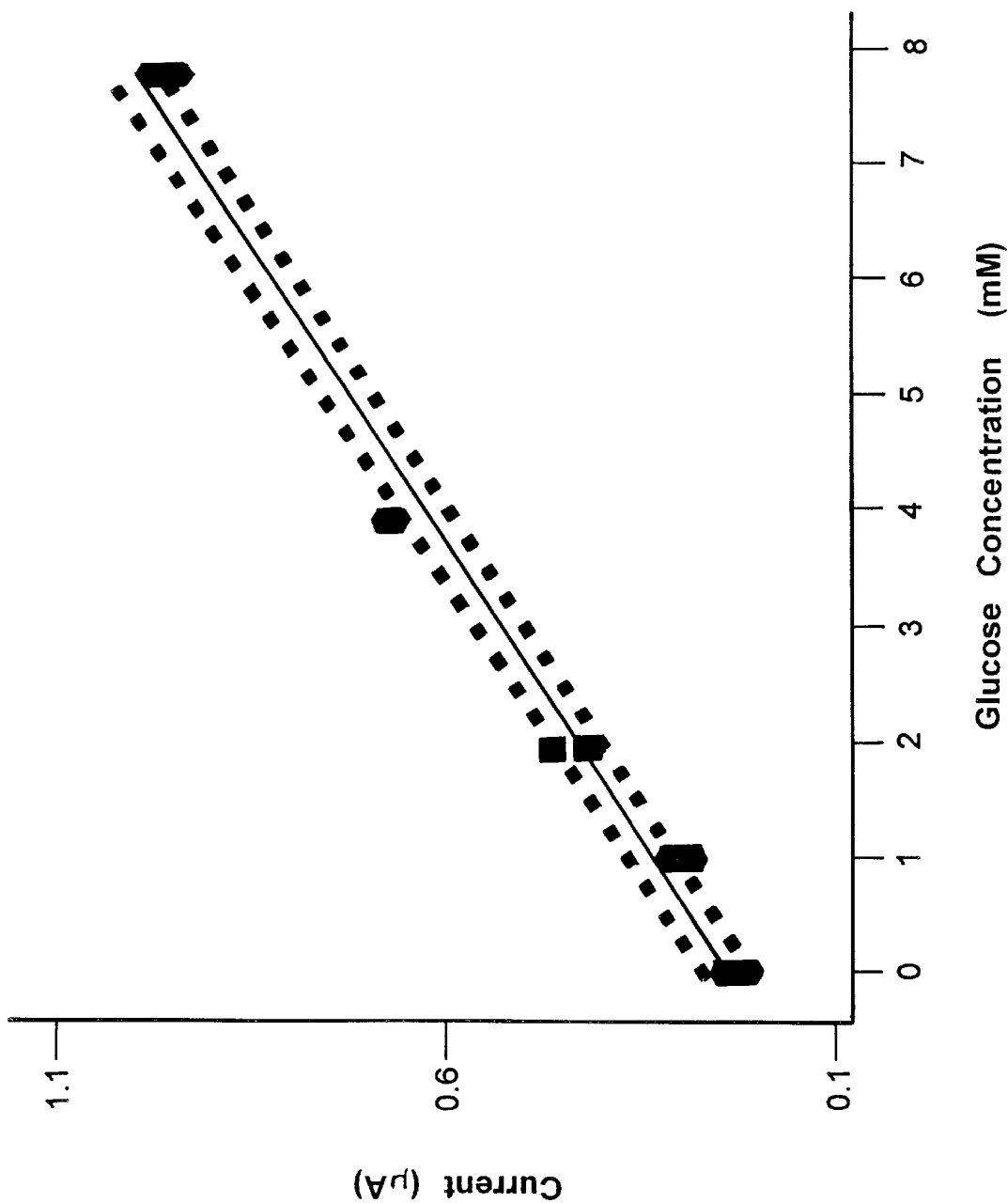
FIG. 14 is a plot of instantaneous current values against glucose concentration showing a linear relationship between current and glucose concentration.

Referring additionally to FIG. 13, actual curves obtained using this method can be seen. From these curves it will be seen that the peak value is many times greater than the steady state value achieved after, for example, 30 microseconds. If one compares the peak values obtained for glucose concentrations of 0, 1, 2, 4 and 8 mM it can be seen that one can easily distinguish between and measure the peak concentrations, whereas the steady state concentrations are so close together as to be almost indistinguishable. Thus, a greatly improved signal to noise ratio is obtained by applying an intermittent voltage and measuring the current obtained at the peak (or shortly thereafter). This greatly enhances the accuracy of measurements which can be made using this type of enzymatic sensor, and it has been found that the response of peak current to glucose concentration is effectively linear. The measurements in FIG. 14 were taken one microsecond after the potential was applied. Each data point therefore represents a single current reading at $t=1$ ms $\mu$s for a given glucose concentration.

Figure 15:
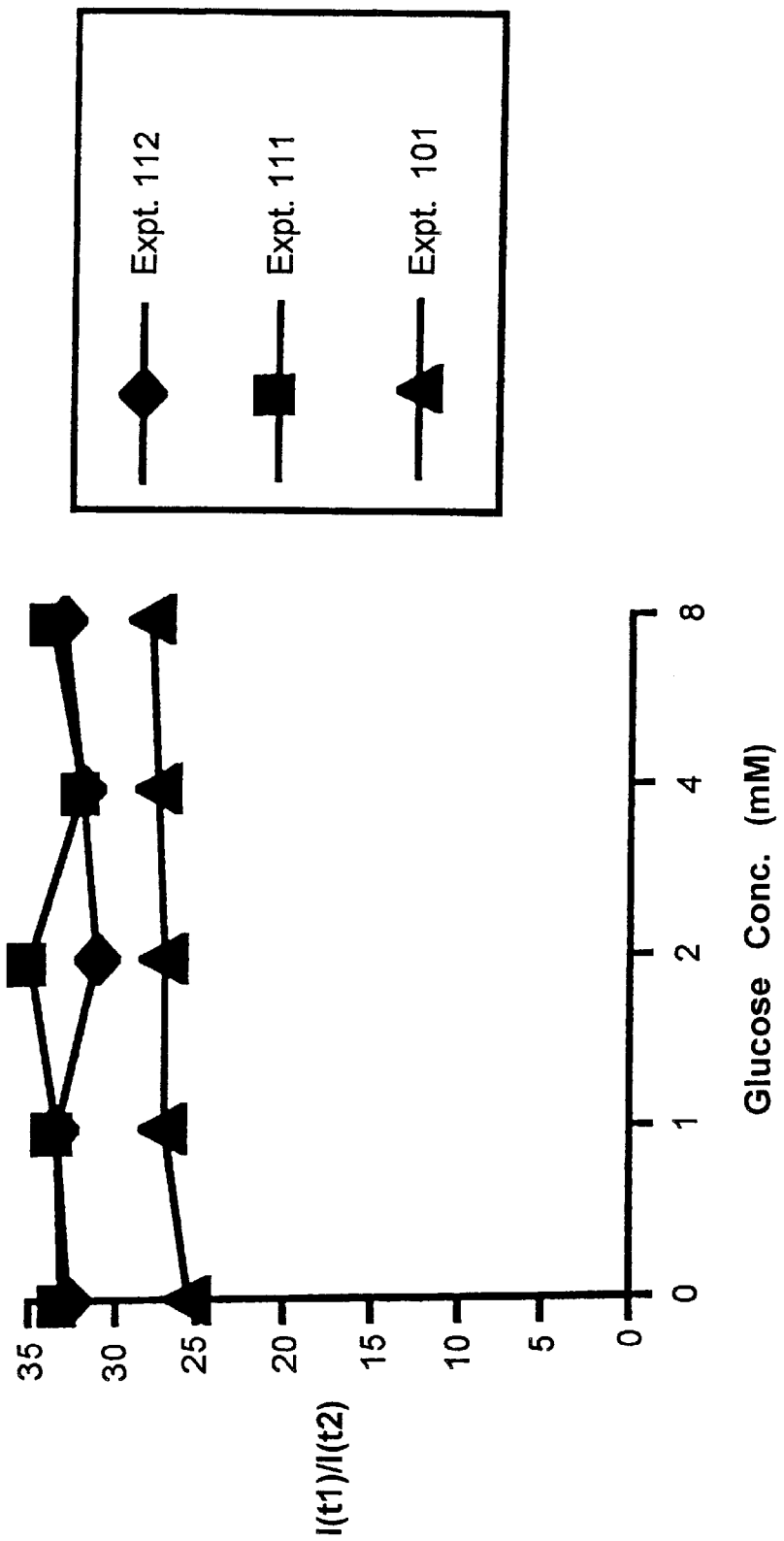
FIG. 15 is a plot of the ratio of two instantaneous current readings taken at different times for various glucose concentrations in respect of three different electrodes, showing how this ratio can be used to evaluate the performance of the electrode.

The performances of the electrodes were evaluated by measuring the currents $I_1$ at $t=1$ $\mu$s and $I_2$ at $t=55$ $\mu$s and then calculating the ratio $I_1/I_2$. This ratio was calculated for each glucose concentration for three different electrodes. One of the electrodes (experiment 101) had degraded and had lost its ability to measure glucose properly, whereas the other two electrodes (experiments 111 and 112) were functioning perfectly. It can be seen that the ratio $I_1/I_2$ in each case is independent of glucose concentration and is equal for the electrodes used in experiments 111 and 112. However, a lower value for $I_1/I_2$ was obtained in experiment 101 and is indicative of the loss of performance. While more sophisticated analytical techniques can be based on the principle used to make the FIG. 15 measurements, FIG. 15 represents a very simple but effective method of continuously monitoring electrode performance. The detecting circuit can be designed to sound an alarm or provide a visual indication when the ratio $I_1/I_2$ changes by an appreciable amount, thereby indicating that the electrode should be replaced.

For best results it has been found advantageous to measure $I_1$ as quickly as possible (e.g. 1–1.5 $\mu$s after the circuit is closed) and to measure $I_2$ when the current has reached steady state (e.g. after 90% of the total connect time has elapsed).

In summary, the "pulse sampling method" described above and illustrated by FIGS. 12–15 provides the following advantages:

(i) the signal is at least two orders of magnitude higher than with a continuous sampling method. Therefore, less amplification is needed, and higher accuracy is achieved.

(ii) the signal to noise ratio is vastly improved; the noise obtained is less than 10% of the signal. In the continuous sampling (or continuous current) method, the noise is higher than the signal itself and its value is eliminated by averaging the samples.

(iii) the pulse sampling method is less sensitive to the presence of substances such as ascorbic acid, uric acid, paracetamoi, etc. The reason for this is that enzymatic detection is effected using two reactions: firstly, the chemical reaction where the analyte is converted and a by-product such as hydrogen peroxide is formed; and secondly, an electrochemical reaction, where hydrogen peroxide is consumed and an electric current flows through the electrodes. The chemical reaction takes place whenever the reactants and enzyme are present, while the electrochemical reaction only takes place when the electrode is at a sufficient potential. At that potential, the abovementioned substances also react with the electrode and induce an undesired current that adds to the current generated by hydrogen peroxide decomposition. When using the pulse sampling method, the voltage is intermittently connected to the electrodes. When disconnected, hydrogen peroxide accumulates at the electrode site but the other substances do not accumulate appreciably during these breaks. Therefore, when reconnecting the potential, there is an "amplification" of the hydrogen peroxide signal compared to the signal resulting from the other substances and therefore their contribution to noise becomes less significant. This "amplification" of the hydrogen peroxide signal relative to the ascorbic acid/uric acid/paracetamol signals would not exist if the voltage was applied continuously.

(iv) The values, gradient and shape of the pulse carry important information about the condition of the sensor. This can be used to monitor the sensor. In prior art electrodes, the degradation of the sensor would only show as an artificially increased or decreased analyte measurement which would be more likely to be wrongly interpreted as an actual measurement than to be interpreted as an indication of sensor degradation. The ability to distinguish between a false signal and a damaged sensor means that the sensor according to the invention is far safer than known sensors for use as a measuring tool.

Figure 16:
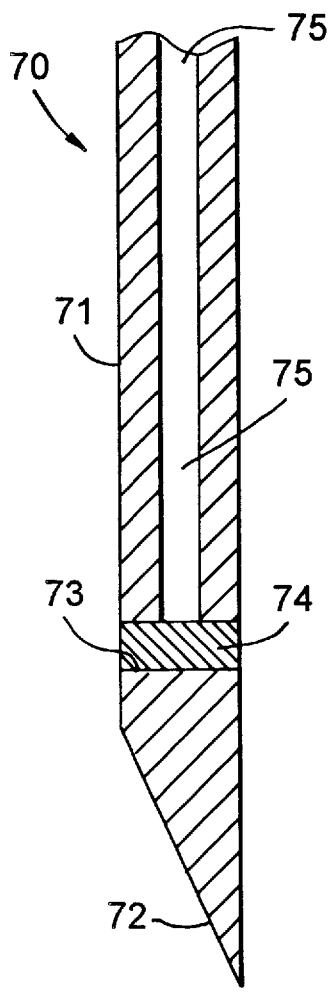
FIG. 16 is a side cross sectional elevation of a further embodiment of sensor needle for use with the device according to the invention.
Figure 17:
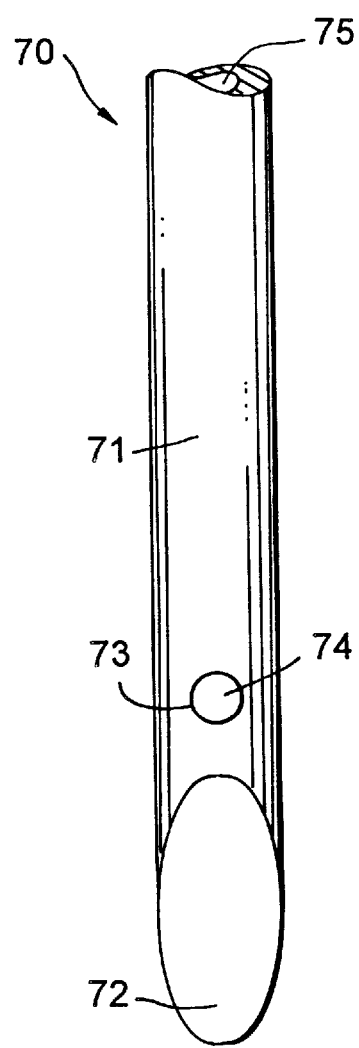
FIG. 17 is a front elevation of the needle of FIG. 16.

In FIGS. 16 and 17, there is indicated, generally at 70, a further embodiment of sensor needle for use with a device according to the invention. The needle 70 comprises a platinum-iridium rod 71 having a bevelled tip 72. The rod 71 is 0.3 mm in diameter.

A transverse bore 73 extends through the thickness of the rod, and bore 73 is filled with an enzyme matrix 74 formed from a casting solution of perflourinated ion exchange membrane ("Nafion"), and glucose oxidase enzyme. A bore 75 extends axially through the length of the rod allowing communication between enzyme matrix 74 and the atmosphere. Bore 75 is 0.1 mm in diameter. Each of bores 73 and 75 can be conveniently formed by laser drilling.

Needle 70 works in exactly the same manner as the needles previously described, but provides an advantage in that the enzyme matrix 74 is provided internally of the needle and not as an external coating. This eliminates any tendency for the enzyme layer to be damaged or scratched during manufacture (i.e. when the needle is affixed to the body of the device).

The invention described and claimed herein is not to be limited in scope by the specific embodiments herein disclosed because these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A device for monitoring the concentration of an analyte in a subject, comprising:

a housing having a lower surface for application to the skin of the subject;

means for holding the housing in position with the lower surface against the subject's skin;

an electrical detection circuit comprising a power source connected across two electrodes mounted on said lower surface and switching means, the circuit being completed upon application of the lower surface to the skin of the subject, one of said electrodes being a sensor needle for penetrating through the epidermis and into the dermis when the lower surface is applied to the skin and having an enzyme associated therewith, said enzyme being specific to the analyte to be detected, and the switching means allowing the current through the circuit to flow intermittently to the sensor needle; and a communication circuit comprising means for measuring the current through said electrical detection circuit, means for calculating the concentration of the analyte from the measured current and communicating means for communicating the calculated concentration to the subject.

2. A device according to claim 1, wherein the enzyme is glucose oxidase and the analyte to be measured is glucose.

3. A device according to claim 1, wherein the sensor needle is a working electrode and the other of said two electrodes is a counter electrode in the form of a platinum surface for contact with the subject's skin.

4. A device according to claim 1, wherein the electrical detection circuit also comprises a reference electrode on the lower surface of the housing, in the form of a silver/silver chloride surface for contact with the subject's skin, and a potentiostat having an operational amplifier which drives a current between the working electrode and the counter electrode.

5. A device according to claim 4, wherein the power source and the sensor needle are connected in series with the positive input of the amplifier and wherein a resistor and the delivery needle are connected in series with the amplifier output, the reference electrode being connected to the negative input of the amplifier.

6. A device according to claim 5, wherein the current through the circuit is determined by measuring the voltage drop across said resistor.

7. A device according to claim 6, wherein a voltmeter connected across said resistor provides a signal determined by the magnitude of the voltage drop and the signal is amplified and supplied to the communicating means.

8. A device according to claim 1, wherein the switching means comprises means for intermittently applying a voltage to the sensor needle.

9. A device according to claim 8, further comprising means for comparing the current at different times.

10. A device according to claim 9, wherein the means for comparing the current at different times is integral with the means for controlling the rate of active discharge.

11. A device according to claim 1, wherein the sensor needle is provided with a conduit permitting communication between the inner skin-contacting end and a source of oxygen.

12. A device according to claim 11, wherein the source of oxygen is the atmosphere.

13. A device according to claim 1, wherein the housing comprises a first part and a second part, the first part comprising the lower surface and the electrodes and the second part comprising the power source and the communication circuit.

14. A device according to claim 13, wherein the first part is detachably mounted on the second part, such that the first part can be disposed of and replaced and the second part can be reused a number of times.

15. A device according to claim 1, wherein the communicating means is activated when the calculated analyte concentration falls outside a predetermined range.

16. A device according to claim 1, wherein the communicating means comprises an audible alarm.

17. A device according to claim 1, wherein the communicating means operates continuously to provide a constant indication of the subject's analyte concentration.

18. A device according to claim 1, wherein the communicating means comprises a visible display of the analyte concentration.

19. A device according to claim 18, wherein the visible display is in the form of a liquid crystal display for indicating the analyte concentration as a numerical value.

20. The device of claim 1 wherein the concentration is communicated to the subject.

21. The device of claim 1 wherein the concentration is communicated to a microprocessor.

22. The device of claim 1 wherein the microprocessor is in communication with a liquid drug delivery device for delivering drug to the subject via the subject's skin, the device containing a liquid drug, whereby the microprocessor controls the rate of discharge of drug via the subject's skin in response to the communication thereto.

* * * * *